United States Patent
Mitsushima et al.

(10) Patent No.: US 10,889,903 B2
(45) Date of Patent: Jan. 12, 2021

(54) OXYGEN-GENERATING ANODE

(71) Applicants: NATIONAL UNIVERSITY CORPORATION YOKOHAMA NATIONAL UNIVERSITY, Yokohama (JP); DE NORA PERMELEC LTD., Fujisawa (JP)

(72) Inventors: Shigenori Mitsushima, Yokohama (JP); Yasutomo Takakuwa, Yokohama (JP); Awaludin Zaenal, Fujisawa (JP); Akihiro Kato, Fujisawa (JP)

(73) Assignees: NATIONAL UNIVERSITY CORPORATION YOKOHAMA NATIONAL UNIVERSITY, Yokohama (JP); DE NORA PERMELEC LTD., Fujisawa (JP)

( * ) Notice: Subject to any disclaimer, the term of this patent is extended or adjusted under 35 U.S.C. 154(b) by 142 days.

(21) Appl. No.: 15/525,419

(22) PCT Filed: Nov. 9, 2015

(86) PCT No.: PCT/JP2015/081518
§ 371 (c)(1),
(2) Date: May 9, 2017

(87) PCT Pub. No.: WO2016/076277
PCT Pub. Date: May 19, 2016

(65) Prior Publication Data
US 2017/0321331 A1    Nov. 9, 2017

(30) Foreign Application Priority Data
Nov. 10, 2014    (JP) ................................. 2014-228096

(51) Int. Cl.
*C25B 11/04* (2006.01)
*C25B 3/04* (2006.01)
(Continued)

(52) U.S. Cl.
CPC .............. *C25B 3/04* (2013.01); *C01B 3/0005* (2013.01); *C01B 13/0207* (2013.01);
(Continued)

(58) Field of Classification Search
CPC ......... C25B 3/02–3/04; C25B 11/0494; C25B 11/084; C25B 11/0478; C25B 11/0442;
(Continued)

(56) References Cited

U.S. PATENT DOCUMENTS 6,802,875 B1    10/2004    Kimbara et al.
2008/0234527 A1    9/2008    Matsumoto et al.
(Continued)

FOREIGN PATENT DOCUMENTS

CN    103069051 A    4/2013
JP    3-240987 A    10/1991
(Continued)

OTHER PUBLICATIONS

International Search Report for PCT/JP2015/081518 (PCT/ISA/210) dated Feb. 2, 2016.
(Continued)

*Primary Examiner* — Alexander W Keeling
(74) *Attorney, Agent, or Firm* — Birch, Stewart, Kolasch & Birch, LLP

(57) ABSTRACT

An anode for oxygen evolution that operates at a small overpotential and in a stable manner, and can be used favorably in an organic chemical hydride electrolytic synthesis apparatus.
An anode 10 for oxygen evolution that evolves oxygen in a sulfuric acid aqueous solution containing a substance to be hydrogenated dissolved at a concentration higher than 1 mg/L, wherein an anode substrate 10a is composed of a valve metal, and an anode catalyst layer 10b containing at least one oxide, nitride or carbide of iridium, and at least one (Continued)

(a)

(b)

oxide, nitride or carbide of at least one metal selected from the group consisting of elements belonging to groups 4, 5 and 13 of the periodic table is formed on the surface of the anode substrate 10a.

4 Claims, 2 Drawing Sheets

(51) Int. Cl.
    *C01B 3/00*       (2006.01)
    *C01B 13/02*     (2006.01)
    *C07C 29/132*   (2006.01)
    *C07C 29/20*    (2006.01)
    *C25B 1/04*     (2006.01)

(52) U.S. Cl.
CPC ........ *C01B 13/0248* (2013.01); *C07C 29/132* (2013.01); *C07C 29/20* (2013.01); *C25B 1/04* (2013.01); *C25B 11/0415* (2013.01); *C25B 11/0431* (2013.01); *C25B 11/0473* (2013.01); *C25B 11/0484* (2013.01); *Y02E 60/32* (2013.01); *Y02E 60/36* (2013.01)

(58) Field of Classification Search
CPC .... C25B 11/0405; C25B 11/00; B01J 21/066; B01J 23/20; B01J 23/468; B01J 23/6486; C22C 5/04; C22C 16/00
See application file for complete search history.

(56) References Cited

U.S. PATENT DOCUMENTS

| | | |
|---|---|---|
| 2009/0025291 A1 | 1/2009 | Ichikawa et al. |
| 2009/0242417 A1 | 10/2009 | Cao et al. |
| 2012/0085571 A1 | 4/2012 | Niksa et al. |
| 2012/0118754 A1* | 5/2012 | Calderara ........... C25B 11/0484 205/224 |
| 2012/0214084 A1* | 8/2012 | Sharman ................... C25B 9/10 429/482 |
| 2013/0306489 A1 | 11/2013 | Calderara et al. |
| 2013/0313127 A1 | 11/2013 | Sato et al. |
| 2014/0110268 A1 | 4/2014 | Jackson et al. |
| 2014/0144774 A1 | 5/2014 | Hirashige et al. |
| 2014/0353148 A1 | 12/2014 | Cao et al. |
| 2014/0374249 A1 | 12/2014 | Cao et al. |
| 2015/0008139 A1 | 1/2015 | Saffron et al. |
| 2017/0292198 A1 | 10/2017 | Mitsushima et al. |

FOREIGN PATENT DOCUMENTS

| | | |
|---|---|---|
| JP | 3561108 B2 | 9/2004 |
| JP | 101550557 A | 10/2009 |
| JP | 2009-263771 A | 11/2009 |
| WO | WO 2012/091128 A1 | 7/2012 |
| WO | WO 2013/100162 A2 | 7/2013 |
| WO | WO 2013/100165 A2 | 7/2013 |
| WO | WO 2013/134220 A1 | 9/2013 |
| WO | WO 2016/047629 A1 | 3/2016 |

OTHER PUBLICATIONS

Written Opinion of the International Searching Authority for PCT/JP2015/081518 (PCT/ISA/237) dated Feb. 2, 2016.
Extended European Search Report, dated Jul. 10, 2018, for European Application No. 15859255.0.

* cited by examiner (a)    (b)

OXYGEN-GENERATING ANODE

TECHNICAL FIELD

The present invention relates to an anode for oxygen evolution (hereafter also referred to as simply "the anode"), and relates more specifically to an anode for oxygen evolution that operates at a small overpotential and in a stable manner, and can be used favorably in an organic chemical hydride electrolytic synthesis apparatus.

BACKGROUND ART

Electrical power consumption in Japan is about 1,000 TWh per year, and because thermal power generation is currently also being used to replace the power previously generated by nuclear power generation, the proportion of power generated by thermal power generation has reached 90%. On the other hand, although it is desirable that renewable energy sources such as solar power, wind power, hydropower and geothermal power generation are used more widely as new energy sources capable of suppressing carbon dioxide emissions, the amount of power generated from these sources currently represents only about 1% of total power generation. Although Japan is blessed with water resources, it cannot be claimed to be an ideal location for solar power or wind power, and is therefore currently forced to rely on the transport and storage of energy sources from overseas. Further, although consideration is being given to the use of wind power generation and large-scale solar power generation to alleviate short-period output fluctuations, applying these sources to the alleviation of medium-term output fluctuations or large-scale energy transport is problematic. Accordingly, it is thought that converting the electrical power from these renewable energy sources to chemical energy may be effective. Processes for converting electrical power directly into chemical energy are electrochemical systems, and secondary cells or so-called accumulators are devices for converting electrical power to chemical energy and then storing that energy, and are widely used.

One example of a promising system based on renewable energy is a system in which large-scale solar power generation or wind power generation systems are established in appropriate locations throughout the world, and the generated energy is converted to an energy carrier, which can then be transported to enable the energy to be consumed domestically. Examples of possible energy carriers include liquid hydrogen and ammonia. Hydrogen is also a potential energy carrier, but because hydrogen is a gas at normal temperature and normal pressure, it suffers from the drawback of requiring special tankers for transport and storage. In light of these circumstances, hydrogen transport and storage methods which employ an organic chemical hydride that uses a hydrocarbon such as cyclohexane, methylcyclohexane or decalin are attracting considerable attention as alternatives to transporting and storing hydrogen. These organic chemical hydrides are liquids at normal temperature and normal pressure, and are easy to handle. In this description, an organic chemical hydride refers to a hydrogenated aromatic compound such as methylcyclohexane that has been formed from an aromatic compound such as toluene by a hydrogenation reaction with hydrogen. By adding hydrogen electrochemically to a raw material organic compound and then dehydrogenating the resulting organic chemical hydride, the organic compound can be stored and transported as an energy carrier instead of hydrogen.

Conventionally, the production of organic chemical hydrides such as methylcyclohexane has been performed by an organic chemical hydride production method in which renewable energy is used to produce hydrogen by water electrolysis, and toluene is then subjected to hydrogen addition in a hydrogenation reactor and converted to methylcyclohexane. However, electrolytic synthesis methods enable direct hydrogen addition, enabling the process to be simplified, suffer minimal efficiency loss regardless of scale, and exhibit excellent adaptability to start-stop operations. Moreover, at comparatively small-scale renewable energy locations, where systems that include high-temperature processes tend to be more likely to suffer from reduced efficiency, superior energy conversion can be achieved, particularly from an efficiency perspective, and the energy can then be loaded into the organic chemical hydride energy storage and transport network.

Much investigation has already been conducted into technology that uses these types of organic chemical hydrides. For example, Patent Document 1 proposes an electrolytic cell that reduces an organic compound having an unsaturated bond. Further, Patent Documents 2 and 3 propose devices for producing hydrogen from an organic compound using a membrane separation apparatus. Moreover, Patent Document 4 proposes a device for producing hydrogen from an organic compound and supplying the hydrogen to a fuel cell. Furthermore, Patent Documents 5 and 6 propose methods for the electrolytic oxidation and reduction of organic compounds.

Further, Patent Document 7 discloses an anode for oxygen evolution having an anode catalyst layer formed from iridium (Ir) and tantalum (Ta). Furthermore, Patent Document 8 discloses an anode in which by providing these types of components with a concentration gradient in the cross-sectional direction, the durability can be improved. Moreover, Patent Document 9 discloses a technique in which a valve metal oxide layer is formed on a catalyst layer composed of Ir and Ta, and oxygen evolution proceeds preferentially in an aqueous solution containing contaminants such as organic substances. Furthermore, Patent Documents 10 and 11 disclose high-performance anodes obtained by subjecting a catalyst having similar components to two heat treatments at different temperatures.

CITATION LIST

Patent Documents

Patent Document 1: International Patent Application No. 2012/091128
Patent Document 2: U.S. Patent Application No. 2008/234527
Patent Document 3: U.S. Patent Application No. 2009/025291
Patent Document 4: U.S. Pat. No. 6,802,875
Patent Document 5: U.S. Patent Application No. 2014/110268
Patent Document 6: International Patent Application No. 2013/134220
Patent Document 7: U.S. Patent Application No. 2012/118754
Patent Document 8: U.S. Patent Application No. 2012/085571
Patent Document 9: U.S. Patent Application No. 2013/306489
Patent Document 10: International Patent Application No. 2013/100165
Patent Document 11: International Patent Application No. 2013/100162

SUMMARY OF INVENTION

Technical Problem

However, the Patent Documents mentioned above relate to oxygen-evolving anodes that are used in electrolytic processes such as plating and electrowinning, wherein these anodes are effective in suppressing anode degradation caused by organic substances that are added intentionally to improve product quality, or unavoidable organic substances that exist in the raw materials. However, in electrolytic cells used in organic chemical hydride electrolytic synthesis apparatus, a cathode chamber into which an organic substance such as toluene flows and an anode chamber in which water is oxidized to produce protons are provided with a membrane disposed therebetween, and therefore the flow of a large amount of organic substances into the anode chamber is unavoidable. A determination as to what type of oxygen-evolving anode is best suited to this type of electrolytic process has yet to be satisfactorily investigated.

Accordingly, an object of the present invention is to provide an anode for oxygen evolution that operates at a small overpotential and in a stable manner, and can be used favorably in an organic chemical hydride electrolytic synthesis apparatus.

Solution to Problem

As a result of intensive investigation aimed at addressing the issues described above, the inventors of the present invention discovered that by providing an anode catalyst layer having a prescribed composition on the surface of an anode for oxygen evolution, the above object could be achieved, enabling them to complete the present invention.

In other words, an anode for oxygen evolution according to the present invention is an anode that evolves oxygen in a sulfuric acid aqueous solution containing a substance to be hydrogenated dissolved at a concentration higher than 1 mg/L, wherein the anode substrate is composed of a valve metal, and an anode catalyst layer containing at least one oxide, nitride or carbide of iridium, and at least one oxide, nitride or carbide of at least one metal selected from the group consisting of elements belonging to groups 4, 5 and 13 of the periodic table is formed on the surface of the anode substrate.

In the anode for oxygen evolution of the present invention, the at least one metal selected from the group consisting of elements belonging to groups 4, 5 and 13 of the periodic table is preferably tantalum. Further, in the anode for oxygen evolution of the present invention, the at least one metal selected from the group consisting of elements belonging to groups 4, 5 and 13 of the periodic table preferably also contains zirconium. Moreover, in the anode for oxygen evolution of the present invention, the iridium content in the anode catalyst is preferably from 33 to 90% by mass relative to the total mass of all oxides, nitrides and carbides of iridium, and all oxides, nitrides and carbides of the at least one metal selected from the group consisting of elements belonging to groups 4, 5 and 13 of the periodic table. Furthermore, in the anode for oxygen evolution of the present invention, an intermediate layer composed of titanium and tantalum is preferably formed between the surface of the anode substrate and the anode catalyst layer. The anode for oxygen evolution of the present invention can be used favorably in an organic chemical hydride electrolytic synthesis apparatus in which the substance to be hydrogenated is toluene and the main product is methylcyclohexane.

Effects of Invention

The present invention is able to provide an anode for oxygen evolution that operates at a small overpotential and in a stable manner, and can be used favorably in an organic chemical hydride electrolytic synthesis apparatus.

DESCRIPTION OF EMBODIMENTS

Embodiments of the present invention are described below in further detail using the drawings.

In the anode for oxygen evolution according to the present invention, the anode substrate is composed of a valve metal, and an anode catalyst layer containing at least one oxide, nitride or carbide of iridium, and at least one oxide, nitride or carbide of at least one metal selected from the group consisting of elements belonging to groups 4, 5 and 13 of the periodic table is formed on the surface of this anode substrate. The at least one metal selected from the group consisting of elements belonging to groups 4, 5 and 13 of the periodic table is preferably selected from among titanium (Ti), zirconium (Zr), hafnium (Hf), vanadium (V), niobium (Nb), tantalum (Ta), aluminum (Al), gallium (Ga) and indium (In). The at least one metal selected from the group consisting of elements belonging to groups 4, 5 and 13 of the periodic table is more preferably tantalum, and most preferably also contains zirconium. In this description, the term "valve metal" refers, for example, to aluminum (Al), chromium (Cr), or titanium (Ti) or the like, as well as alloys of these metals, and means a metal that readily forms a passive state. By providing the above anode catalyst layer on the surface of the anode substrate composed of a valve metal, oxygen evolution can be conducted efficiently even in a sulfuric acid aqueous solution in which the substance to be hydrogenated is dissolved in a concentration higher than 1 mg/L. The anode for oxygen evolution of the present invention can be used particularly favorably in an electrolytic cell for producing an organic chemical hydride which uses toluene as the substance to be hydrogenated, and in which the main product is methylcyclohexane.

In the anode of the present invention, the Ir content in the anode catalyst is preferably from 33 to 90% by mass relative to the total mass of all oxides, nitrides and carbides of iridium, and all oxides, nitrides and carbides of the at least one metal selected from the group consisting of elements belonging to groups 4, 5 and 13 of the periodic table. By ensuring that the Ir content satisfies this range, oxygen evolution can be conducted particularly efficiently.

Figure 1:
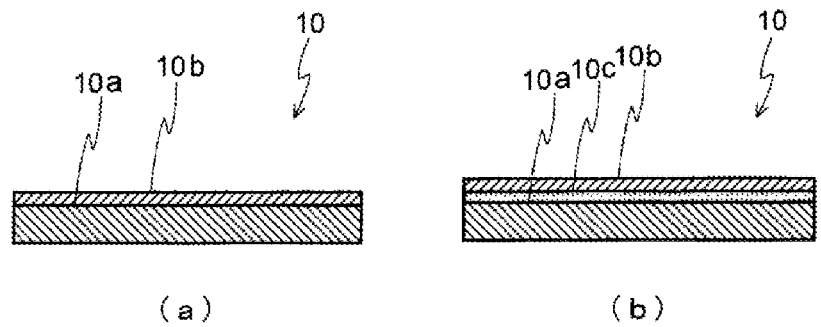
FIG. 1 illustrates examples of cross-sectional views of anodes for oxygen evolution according to the present invention, wherein (a) illustrates an anode in which the anode catalyst layer is provided directly on the anode substrate, and (b) illustrates an anode in which an intermediate layer is formed between the anode substrate and the anode catalyst layer.

Further, in the anode of the present invention, an intermediate layer composed of Ti and Ta is preferably formed between the surface of the anode substrate and the anode catalyst layer. FIG. 1 illustrates examples of cross-sectional views of anodes for oxygen evolution according to the present invention, wherein FIG. 1(a) illustrates an anode in which the anode catalyst layer is provided directly on the anode substrate, and FIG. 1(b) illustrates an anode in which an intermediate layer is formed between the anode substrate and the anode catalyst layer. In the anode 10 of the present invention, the anode catalyst layer 10b may be formed directly on the surface of the anode substrate 10a, as illustrated in FIG. 1(a), but it is preferable that an intermediate layer 10c composed of Ti and Ta is formed on the surface of the anode substrate 10a, and the anode catalyst layer 10b is then formed on the surface of this intermediate layer, as illustrated in FIG. 1(b).

This is because forming a layer composed of Ti—Ta as the intermediate layer 10c is able to suppress corrosion of the anode substrate 10a, which tends to proceed during electrolysis. In the anode 10 of the present invention, the thickness of the intermediate layer 10c is preferably from 0.1 to 10 µm, and an anode in which the anode catalyst layer 10b containing an oxide, nitride or carbide of Ir and an oxide, nitride or carbide of at least one metal selected from the group consisting of elements belonging to groups 4, 5 and 13 of the periodic table is formed in an amount equivalent to an Ir content per unit area of the electrode of 1 to 40 g/m$^2$ can be used particularly favorably as the anode 10.

In order to avoid any increase in resistance caused by gas bubbles generated during electrolysis, and promote supply of the electrolyte, the anode 10 of the present invention is preferably a porous body having excellent corrosion resistance relative to acidic electrolytes. Accordingly, a titanium expanded mesh can be used very favorably as the anode substrate 10a. Because the expanded mesh adopts a three-dimensional structure after mesh processing, the mesh is preferably subjected to an appropriate flattening treatment. The ideal thickness range for the expanded mesh is from 0.1 to 2 mm, and it is preferable that the distance between centers in the short direction is from 0.1 to 4 mm, the distance between centers in the long direction is from 0.1 to 6 mm, and the aperture ratio is about 30 to 70%.

The anode 10 of the present invention can be produced by subjecting the surface of the valve metal such as Ti that forms the anode substrate 10a to a dry blast treatment, subsequently performing a washing treatment in an aqueous solution of 20% sulfuric acid or the like, and then performing a plurality of repetitions of a process in which a mixed aqueous solution prepared by dissolving Ir and at least one metal selected from the group consisting of elements belonging to groups 4, 5 and 13 of the periodic table is applied to the substrate and a heat treatment is then performed in an electric furnace at 370 to 550° C. During production of the anode 10, in those cases where an intermediate layer 10c is to be provided between the surface of the anode substrate 10a and the anode catalyst layer 10b, an arc ion plating device may be used to form the intermediate layer 10c such as a Ti—Ta layer on the surface of the anode substrate 10a following the washing treatment in the aqueous solution of 20% sulfuric acid or the like. A plurality of repetitions of the process in which a mixed aqueous solution prepared by dissolving Ir and at least one metal selected from the group consisting of elements belonging to groups 4, 5 and 13 of the periodic table is applied and a heat treatment is then performed in an electric furnace at 370 to 550° C. may then be performed to compete production of the anode 10.

[Electrolytic Cell for Producing Organic Chemical Hydride]

Figure 2:
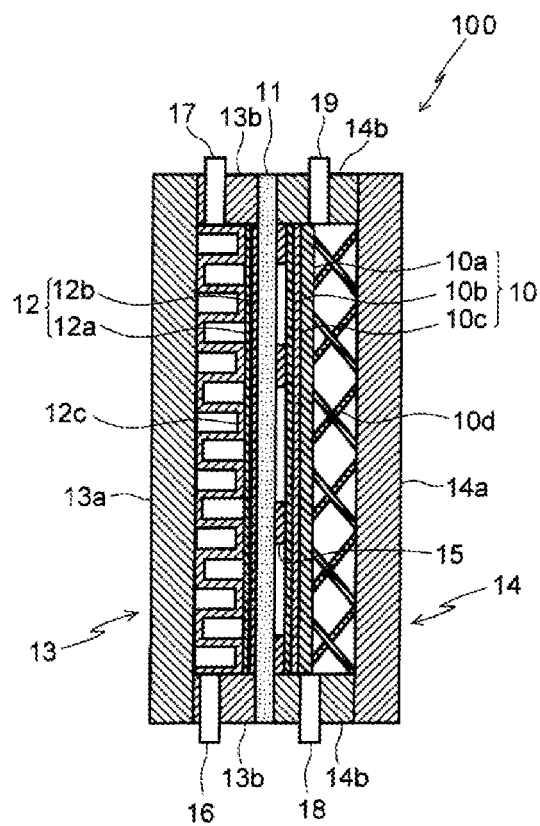
FIG. 2 is a schematic structural view of an electrolytic cell for producing an organic chemical hydride that uses an anode for oxygen evolution according to a preferred embodiment of the present invention.

Next is a description of an electrolytic cell for producing an organic chemical hydride that uses the anode for oxygen evolution according to the present invention. FIG. 2 is a schematic structural view of an electrolytic cell for producing an organic chemical hydride that uses an anode for oxygen evolution according to a preferred embodiment of the present invention. The organic chemical hydride-producing electrolytic cell 100 according to the present invention (the electrolytic cell 100) contains the anode 10 for oxygen evolution of the present invention, and also includes a solid polymer electrolyte membrane (hereafter also abbreviated as "the electrolyte membrane") 11 that has proton conductivity, a cathode 12 which is provided on one surface of the electrolyte membrane 11 and reduces the substance to be hydrogenated to produce a hydride, a cathode chamber 13 which houses the cathode 12 and is supplied with the substance to be hydrogenated, the anode 10 of the present invention which is provided on the other surface of the electrolyte membrane 11 and oxidizes water to produce protons, and an anode chamber 14 which houses the anode 10 and is supplied with an electrolytic solution. In the example illustrated in the drawing, the cathode 12 is composed of a cathode substrate 12a and a cathode catalyst layer 12b formed on the surface of the cathode substrate.

Further, in the illustrated example, the cathode chamber 13 is formed from an outermost partition plate 13a and a spacer 13b positioned between the peripheral rim of this partition plate 13a and the electrolyte membrane 11, and a cathode support 12c is interposed between the partition plate 13a and the cathode 12. Further, the anode chamber 14 is formed from an outermost partition plate 14a and a spacer 14b positioned between the peripheral rim of this partition plate 14a and the electrolyte membrane 11. Moreover, an anode-supporting elastic body 10d is disposed between the partition plate 14a and the anode 10, and an anode spacer 15 is disposed between the anode 10 and the electrolyte membrane 11. Furthermore, in the illustrated example, an inlet 16 for the substance to be hydrogenated is provided at the bottom of the cathode chamber 13, and a hydride outlet 17 is provided at the top of the cathode chamber 13, whereas an acidic electrolytic solution inlet 18 is provided at the bottom of the anode chamber 14, and an acidic electrolytic solution outlet 19 is provided at the top of the anode chamber 14. The structure of the electrolytic cell of the present invention is described below in further detail.

[Solid Polymer Electrolyte Membrane]

The electrolyte membrane 11 is formed from a material (ionomer) having proton conductivity, and allows selective transmission of protons while inhibiting mixing or diffusion of substances between the cathode 12 and the anode 10. The thickness of the electrolyte membrane 11 is preferably from 5 to 300 µm, more preferably from 10 to 200 µm, and most preferably from 20 to 100 µm. If the thickness of the electrolyte membrane 11 is less than 5 µm, then the barrier properties of the electrolyte membrane 11 deteriorate, and cross leakage is more likely to occur. Further, if the thickness of the electrolyte membrane 11 exceeds 300 µm, then the ion transport resistance becomes excessively large, which is also undesirable.

[Cathode]

In the electrolytic cell 100 of the present invention, as illustrated in the drawing, the cathode 12 may be constructed of the cathode substrate 12*a* and the cathode catalyst layer 12*b*. Examples of materials that may be used as the cathode substrate 12*a*, which constitutes part of the cathode 12 of the electrolytic cell 100 according to the present invention, include fibrous sintered bodies such as cloth and paper formed from a porous conductive substrate of carbon. The reason for using a porous conductive substrate is because it is preferable to have an appropriate degree of porosity to enable the supply and removal of gases and liquids, while ensuring a satisfactory level of conductivity. Substrates having a thickness of 0.01 to 5 mm, a porosity of 30 to 95% and a representative pore size of 0.001 to 1 mm are particularly preferred. Incorporating a metal component on the surface of this cathode substrate 12*a* is also preferred, as it improves the conductivity of the overall conductive layer and enables a more uniform current to be achieved.

Carbon cloth is a cloth woven from bundles containing several hundred fine carbon fibers having a diameter of several µm, and is ideal as the cathode substrate 12*a* due to its excellent gas-liquid permeability. Further, carbon paper is prepared by using a papermaking method to form a thin-film precursor from raw carbon fiber and then sintering the precursor, and this type of carbon paper can also be used favorably. If power is supplied directly to this type of carbon-based conductive substrate, then because of the insufficient conductivity, localized current concentration may occur, and this locally concentrated current may then be supplied to the gas diffusion layer or reaction layer, causing a deterioration in the electrolysis efficiency, but by also incorporating a metal component, current can be supplied more uniformly to the conductive substrate.

[Cathode Catalyst]

Examples of the types of cathode catalysts that can be used include particles of metals selected from among platinum (Pt), ruthenium (Ru), palladium (Pd), Ir, and alloys of these metals. Commercially available particles of these metals may be used, or particles that have been synthesized in accordance with conventional methods may be used. For example, the synthesis may either employ a wet method in which a reducing agent is mixed with an aqueous solution containing dissolved catalyst metal ions to synthesize metal particles, or employ a dry method that uses deposition or sputtering. The particle size of the cathode catalyst particles is preferably from 0.001 to 1 µm.

Although cathode catalyst particles need not necessarily be supported on the cathode substrate 12*a*, by using carbon particles as the carrier particles and expanding on these particles, the catalyst surface area can be increased effectively. Carbon microparticles are usually used as the carrier particles, and furnace black or acetylene black or the like can be used. The particle size of the carbon microparticles is preferably from 0.01 to 1 µm. The conductive powder in the reaction layer has the function of suppressing aggregation of the hydrophilic catalyst particles.

[Cathode Production]

There are no particular limitations on the method used for producing the cathode 12. For example, by mixing a catalyst component powder, a hydrophobic resin, water, a solvent such as naphtha, and a dispersion DE521 (manufactured by DuPont Corporation) of the ionomer Nafion (a registered trademark), so that the ratio of the mass following drying relative to the mass of carbon in the catalyst is within a range from 1:10 to 10:1, and then using an appropriate solvent, a coatable catalyst ink can be prepared. Subsequently, this catalyst ink is applied to the cathode substrate 12*a*, and is then dried and fired to fix the particles of the cathode catalyst to the cathode substrate 12*a*. The ionomer of the Nafion dispersion is effective in maintaining the electron transfer reaction in the non-conductive organic hydride compound inside the porous structure. The hydrophobic resin (fluorine component) is a gas-permeable material, and the particle size of the hydrophobic resin powder is preferably from 0.005 to 10 µm. The application, drying and firing are preferably repeated multiple times, as this yields a more uniform cathode catalyst layer 12*b*. In this manner, the cathode 12 having the cathode catalyst layer 12*b* can be produced.

In the electrolytic cell 100 according to the present invention, a catalyst ink component may also be used to form a cathode catalyst layer on the electrolyte membrane 11. A bar coater application method may be used to form a cathode catalyst layer on one surface of the electrolyte membrane 11, thus forming a cathode-electrolyte membrane composite. This catalyst ink is spray coated onto the electrolyte membrane 11 so that the combined mass of Pt and Ru in the catalyst per unit area of the electrode reaches 0.5 mg/cm$^2$, and the solvent component in the ink can then be dried to obtain an electrolyte membrane-catalyst assembly.

The cathode substrate 12*a* is used with a pressure applied in the thickness direction, and it is undesirable if the conductivity in the thickness direction changes as a result of this pressure. In order to obtain a cathode having improved performance and a packing ratio of 20 to 50%, press working is preferably performed. Press working is performed to enhance the conductivity by compressing the carbon material, and to stabilize any changes in the packing ratio and conductivity when pressure is applied during use. An improvement in the degree of bonding between the cathode catalyst layer 12*b* and the cathode substrate 12*a* also contributes to an improvement in the conductivity. Further, as a result of compression of the cathode substrate 12*a* and the reaction layer, and an improvement in the degree of bonding between the cathode catalyst layer 12*b* and the cathode substrate 12*a*, the ability to supply the raw material substance and remove the product substance is also enhanced. Conventional apparatus such as hot presses or hot rollers can be used as the press working apparatus. The press working conditions preferably include a temperature of room temperature to 360° C. and a pressure of 0.1 to 5 MPa. The above procedure enables the production of a cathode 12 having high levels of conductivity and reactivity.

[Cell Structure]

In the electrolytic cell 100 of the present invention illustrated in FIG. 2, the partition plate 13*a* having electron conductivity is disposed at the outermost portion of the cathode chamber 13. The partition plate 13*a* is, for example, formed from a metal such as stainless steel. The spacer 13*b* is fitted between the peripheral rim of this partition plate 13*a* and the electrolyte membrane 11, and the space enclosed by the partition plate 13*a*, the spacer 13*b* and the electrolyte membrane 11 functions as the cathode chamber 13. The spacer 13*b* also functions as a sealing material that prevents the substance to be hydrogenated and the organic substance containing the hydride from leaking out of the cathode chamber 13, and preferably has electronic insulating properties. Examples of the material used for the spacer 13*b* include ethylene tetrafluoride resins.

In the example illustrated in the drawing, the inlet 16 for the substance to be hydrogenated is provided in a lower portion of the spacer 13*b*, and the substance to be hydrogenated such as toluene is supplied to the cathode chamber 13 through this inlet 16. Further, the hydride outlet 17 is provided in an upper portion of the spacer 13b, and the organic substance containing hydrides such as methylcyclohexane, which is a hydride of toluene, is discharged to the outside of the system through this hydride outlet 17.

Further, in the illustrated example, the cathode support 12c is disposed between the partition plate 13a and the cathode 12. As described below, the cathode support 12c is exposed to a pressing force by the anode-supporting elastic body 10d, and ensures favorable electron conductivity between the partition plate 13a and the cathode 12. Furthermore, the cathode support 12c also forms flow channels that control the flows of the substance to be hydrogenated and the hydride.

The partition plate 14a having electron conductivity is disposed on the outer portion of the anode chamber 14 of the electrolytic cell 100 of the present invention. The partition plate 14a is, for example, formed from a metal such as titanium. The spacer 14b is fitted between the peripheral rim on the anode 10 side of this partition plate 14a and the electrolyte membrane 11, and the space enclosed by the partition plate 14a, the spacer 14b at the end portions on the side of the anode chamber 14, and the electrolyte membrane 11 functions as the anode chamber 14. The spacer 14b also functions as a sealing material that prevents the acidic electrolytic solution from leaking out of the anode chamber 14, and preferably has electronic insulating properties. Examples of the material used for the spacer 14b include ethylene tetrafluoride resins.

In the illustrated example, the acidic electrolytic solution inlet 18 is provided in a lower portion of the spacer 14b, and the acidic electrolytic solution is supplied to the anode chamber 14 through this acidic electrolytic solution inlet 18. Examples of the acidic electrolytic solution include solutions of sulfuric acid, phosphoric acid, nitric acid or hydrochloric acid having an ion conductance measured at 20° C. of at least 0.01 S/cm. If the ion conductance of the acidic electrolytic solution is lower than 0.01 S/cm, then an industrially adequate electrochemical reaction is difficult to achieve. Further, an acidic electrolytic solution outlet 19 is provided in an upper portion of the spacer 14b, and the acidic electrolytic solution stored in the anode chamber 14 is discharged from the system through this acidic electrolytic solution outlet 19.

Furthermore, in the illustrated example, the anode-supporting elastic body 10d is disposed between the anode 10 and the partition plate 14a, and the anode 10 is pressed against the electrolyte membrane 11 by the anode-supporting elastic body 10d. The anode-supporting elastic body 10d is, for example, formed form an electronic conductor having a plate spring or coil structure. In the illustrated example, the anode spacer 15 is interposed between the anode 10 and the electrolyte membrane 11, and this anode spacer 15 is structured to maintain a prescribed gap between the anode 10 and the electrolyte membrane 11. In this manner, by employing a structure in which the anode-supporting elastic body 10d is provided between the partition plate 14a and the anode 10 that constitute the anode chamber 14 so as to hold the anode 10, maintenance operations such as replacing the anode 10 can be performed more easily.

The anode-supporting elastic body 10d is preferably formed from a material having acid resistance to the acidic electrolytic solution that is introduced through the acidic electrolytic solution inlet 18, and titanium or a titanium alloy can be used favorably as a base material. Various types of structures may be considered for the structure of the elastic body that constitutes the anode-supporting elastic body 10d, including V-shaped springs, X-cross springs, cushion coils, and an aggregate of fibers produced by chatter vibration cutting. The thickness and the like of the material may be selected as appropriate, with due consideration of the contact resistance of each member, so as to achieve the required contact pressure.

EXAMPLES

The present invention is described below in further detail using a series of examples, but these examples are merely illustrations designed to better describe the present invention, and in no way limit the present invention.

Example 1

[Anode Substrate Pretreatment]

A Ti plate with a thickness of 3 mm was used as the anode substrate. The surface of this substrate was subjected to a dry blast treatment using an iron grid (#120 size), and the anode substrate was then subjected to an acid wash treatment for 10 minutes in a 20% sulfuric acid aqueous solution (105° C.). The washed anode substrate was set in an arc ion plating apparatus, and an arc ion plating coating of a pure titanium material was formed. The coating conditions were as follows.

Target: JIS class 1 titanium circular plate (backside cooled with water)
Degree of vacuum: 1.3 Pa (with Ar gas introduction and substitution)
Power input: 500 W (3.0 kV)
Substrate temperature: 150° C. (during arc ion plating)
Time: 35 minutes
Coating thickness: 2 μm (calculated as mass increase)

When an X-ray diffraction measurement was performed after arc ion plating coating, a sharp crystalline peak attributable to the substrate bulk and a broad pattern attributable to the sputtering coating were observed, confirming that the coating was amorphous.

[Preparation of Ir-85% by Mass/Ta-15% by Mass Catalyst]

Next, iridium tetrachloride and tantalum pentachloride were dissolved in 35% hydrochloric acid so as to achieve a ratio of 85% by mass Ir and 15% by mass Ta. This coating solution was applied with a brush to the anode substrate for which the arc ion plating coating treatment had been completed, and following drying, the coated substrate was subjected to a thermal decomposition coating process in an air circulating electric furnace (550° C., 20 minutes) to form an anode catalyst layer composed of a solid solution of iridium oxide and tantalum oxide. The coating thickness per single brush application was set so that the volume of coating solution was equivalent to an amount of iridium of approximately 1.0 g/m$^2$. This series of operations from application to firing was repeated 12 times.

[Method for Testing the Effect of Toluene]

An electrolytic solution containing 50 g/L of sulfuric acid was prepared, and using zirconium (Zr) as the cathode, electrolysis was performed at a temperature of 50° C. and a current density of 0.4 A/cm$^2$, and the potential at the anode was measured against a mercurous sulfate reference electrode. Next, the above electrolytic solution was saturated with toluene (TL) (500 mg/L) to prepare an electrolytic solution, the potential was measured under these conditions, and the potential difference due to the absence or presence of TL was measured.

[Test Results for Ir—Ta System]

The presence of toluene caused an increase in the potential of only 6 mV.

Example 2

With the exception of altering the anode firing temperature to 460° C., this example was performed under all the same conditions as Example 1. The results revealed an increase in the potential of only 8 mV.

Example 3

With the exception of altering the anode firing temperature to 370° C., this example was performed under all the same conditions as Example 1. The results revealed an increase in the potential of only 8 mV.

Example 4

With the exceptions of altering the Ir:Ta compositional ratio within the anode to 65:35 (% by mass) and altering the firing temperature to 550° C., this example was performed under all the same conditions as Example 1. The results revealed an increase in the potential of only 4 mV.

Example 5

With the exceptions of altering the Ir:Ta compositional ratio within the anode to 65:35 (% by mass) and altering the firing temperature to 370° C., this example was performed under all the same conditions as Example 1. The results revealed an increase in the potential of only 1 mV.

Example 6

With the exceptions of altering the Ir:Ta compositional ratio within the anode to 50:50 (% by mass) and altering the firing temperature to 550° C., this example was performed under all the same conditions as Example 1. The results revealed an increase in the potential of only 5 mV.

Example 7

With the exceptions of altering the Ir:Ta compositional ratio within the anode to 50:50 (% by mass) and altering the firing temperature to 370° C., this example was performed under all the same conditions as Example 1. The results revealed an increase in the potential of only 1 mV.

Example 8

With the exceptions of altering the Ir:Ta compositional ratio within the anode to 33:67 (% by mass) and altering the firing temperature to 550° C., this example was performed under all the same conditions as Example 1. The results revealed no increase in the potential.

Example 9

With the exceptions of altering the Ir:Ta compositional ratio within the anode to 33:67 (% by mass) and altering the firing temperature to 370° C., this example was performed under all the same conditions as Example 1. The results revealed an increase in the potential of only 2 mV.

Comparative Example 1

[Preparation of Ir-100% by Mass Anode Catalyst]

A coating solution was prepared by dissolving iridium tetrachloride in 35% hydrochloric acid, this coating solution was applied with a brush to the anode substrate for which the arc ion plating coating treatment had been completed, and following drying, the coated substrate was subjected to a thermal decomposition coating process in an air circulating electric furnace (550° C., 20 minutes) to form an anode catalyst layer of iridium oxide. The coating thickness per single brush application was set so that the volume of coating solution was equivalent to an amount of iridium of approximately 1.0 g/m$^2$. This series of operations from application to firing was repeated 12 times. The change in the potential of the thus prepared anode was tested using the same method as Example 1. The results revealed an increase in the potential of 43 mV.

Comparative Example 2

With the exception of altering the anode firing temperature to 370° C., this example was performed under all the same conditions as Comparative Example 1. The results revealed an increase in the potential of 22 mV.

Comparative Example 3

[Preparation of Ir-50% by Mass/Pt-50% by Mass Anode Catalyst]

A coating solution was prepared by dissolving iridium tetrachloride and platinum chloride in 35% hydrochloric acid, this coating solution was applied with a brush to the anode substrate for which the arc ion plating coating treatment had been completed, and following drying, the coated substrate was subjected to a thermal decomposition coating process in an air circulating electric furnace (550° C., 20 minutes) to form an anode catalyst layer composed of a solid solution of iridium oxide and platinum. The coating thickness per single brush application was set so that the volume of coating solution was equivalent to an amount of metal of approximately 1.0 g/m$^2$. This series of operations from application to firing was repeated 12 times. The change in the potential of the thus prepared anode was tested using the same method as Example 1. The results revealed an increase in the potential of 49 mV.

Comparative Example 4

[Preparation of Ir-70% by Mass/Sn-30% by Mass Anode Catalyst]

A coating solution was prepared by dissolving iridium tetrachloride and stannous oxalate in 35% hydrochloric acid, this coating solution was applied with a brush to the anode substrate for which the arc ion plating coating treatment had been completed, and following drying, the coated substrate was subjected to a thermal decomposition coating process in an air circulating electric furnace (550° C., 20 minutes) to form an anode catalyst layer composed of a solid solution of iridium oxide and tin oxide. The coating thickness per single brush application was set so that the volume of coating solution was equivalent to an amount of iridium of approximately 1.0 g/m$^2$. This series of operations from application to firing was repeated 12 times. The change in the potential of the thus prepared anode was tested using the same method as Example 1. The results revealed an increase in the potential of 33 mV.

Example 10

In Example 10, the effect of Zr addition was evaluated. A solution prepared by dissolving $H_2IrCl_6 \cdot 6H_2O$, $Ta(C_4H_9O)_5$ and $Zr(C_4H_9O)_4$ in n-butanol was used as a precursor for forming an $Ir_xTa_yZr_zO_2/Ti$ electrode. The compositional ratio of the precursor solution was set to an Ir:Ta:Zr molar ratio of 7:2:1 or 7:1:2. The Ti substrate was subjected to surface polishing and then an etching treatment for 20 minutes in 20% by mass HCl as pretreatments. The precursor solution was applied to the Ti substrate by dip coating, and following drying, a thermal decomposition treatment was performed in the air at 500° C. This series of operations was repeated 20 times, and then a final heat treatment was performed at 500° C. for one hour.

In a three-electrode cell using the prepared electrode as the working electrode, a reversible hydrogen electrode (RHE) as the reference electrode, and a platinum coil as the counter electrode, electrochemical measurements were performed using 1.0 M $H_2SO_4$ and a toluene-saturated 1.0 M $H_2SO_4$ as the electrolyte. The test temperature was 60° C. Cyclic voltammetry (CV) was performed at 0.3 to 1.1 V vs. RHE and 200 mVs$^{-1}$ as a pretreatment, and Slow Scan Voltammetry (SSV) was then conducted at 1.0 to 2.0 V vs. RHE and 5 mVs$^{-1}$ and the overpotential was evaluated. Using a 1.0 M $H_2SO_4$ saturated with toluene and benzyl alcohol, which represents an oxide of toluene, as the electrolyte, the change over time in the voltage of a two-electrode cell using the prepared electrode as the working electrode and a platinum mesh as the counter electrode was evaluated.

Figure 3:
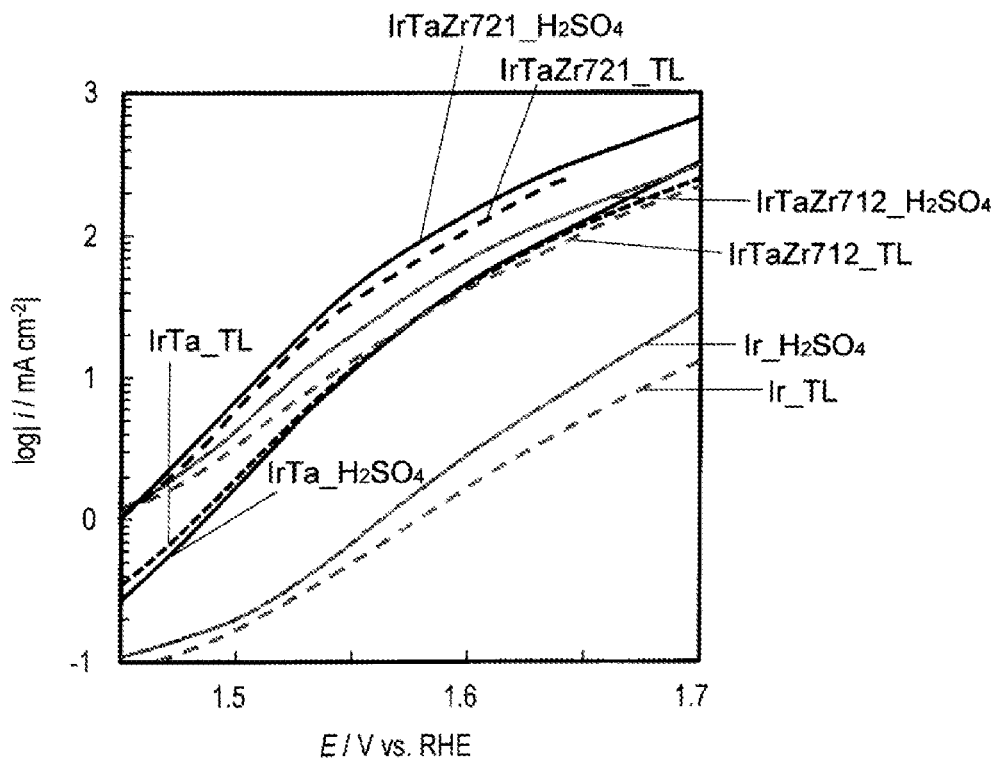
FIG. 3 is a graph illustrating the relationship between the potential and the current density dependence when electrolysis is conducted using the anode of Example 10.

FIG. 3 illustrates the relationship between the potential and the current density dependence when electrolysis was conducted using the anode of Example 10. As reference, the results for an Ir—Ta (1:1) electrode prepared in a similar manner and an Ir (100%) electrode are also shown. In each case, an increase in the potential was observed in the sulfuric acid aqueous solution containing added toluene, but the potential for Example 10 was lower than the other electrodes, indicating superior performance. In FIG. 3, the solid lines represent the results using the aqueous solution containing only sulfuric acid as the electrolyte, the dashed lines represent the results using the aqueous solution of sulfuric acid containing added toluene, IrTaZr721 means the composition in which Ir:Ta:Zr=7:2:1, and IrTaZr712 means the composition in which Ir:Ta:Zr=7:1:2. Based on FIG. 3, it is evident that the Ir:Ta:Zr compositional ratio of 7:2:1 yielded excellent results.

Figure 4:
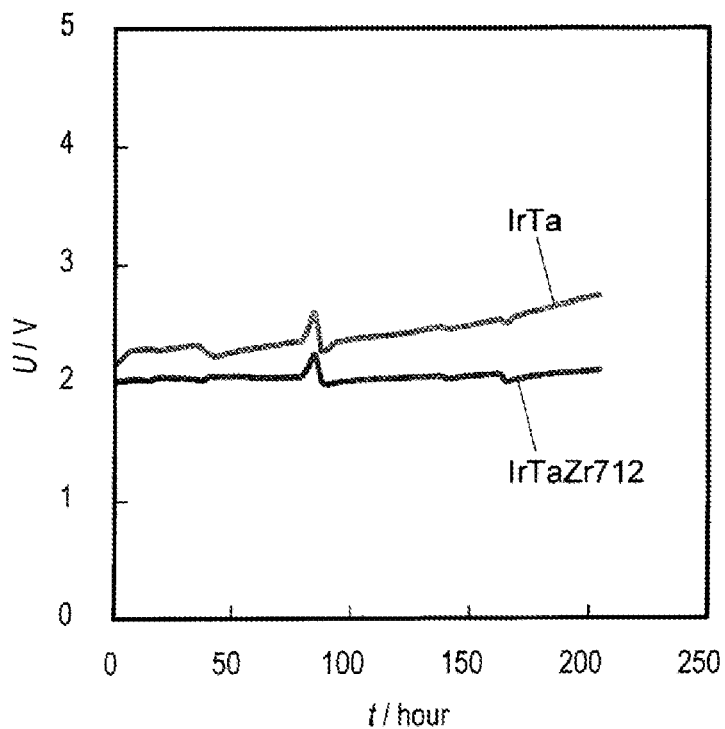
FIG. 4 is a graph illustrating the change in cell voltage upon continuous electrolysis for 200 hours using the anode of Example 10 and the anode of Example 1.

FIG. 4 illustrates the change in cell voltage upon continuous electrolysis for 200 hours using the anode of Example 10 and the anode of Example 1. The electrode of Example 10 exhibited a stable cell voltage, and it is evident that incorporating Zr in the anode catalyst layer stabilizes the cell voltage.

Example 11

A structure was prepared in accordance with the organic chemical hydride production apparatus (electrolytic cell) illustrated in FIG. 2, under the same conditions as Example 1.

Using an NRE212CS membrane (manufactured by DuPont Corporation, thickness: 51 μm) as the electrolyte membrane, a cathode catalyst layer was formed on the treated surface of the electrolyte membrane using a bar coater application method, thus forming a cathode-electrolyte membrane composite. In the formation of the cathode catalyst layer, a dispersion DE521 (manufactured by DuPont Corporation) of the ionomer Nafion (a registered trademark) was first added to a powder of a PtRu/C catalyst TEC61E54E (manufactured by Tanaka Kikinzoku Kogyo K.K., platinum (Pt): 23% by mass, Ru: 27% by mass) so that the ratio of the mass following drying relative to the mass of carbon in the catalyst was 4:5, and an appropriate solvent was then used to prepare a coatable ink. This ink was spray coated onto the electrolyte membrane so that the total mass of Pt and Ru in the catalyst per unit are of the anode was 0.5 mgcm$^{-2}$, and the solvent component in the ink was then dried at 70° C. to obtain a cathode catalyst layer.

A cathode diffusion layer SGL35BC (manufactured by SGL Carbon AG) that had been cut to size to match the anode surface was affixed to the surface of the cathode catalyst layer, and thermal bonding was performed at 120° C. and 1 MPa for 2 minutes to form a cathode-electrolyte membrane composite.

A carbon-based structure obtained by molding a carbon/epoxy resin mixture was used as a structure representing the cathode partition plate bonded to the cathode support. The cathode support portion of this structure had a plurality of flow channels to facilitate liquid circulation formed in the surface of the cathode support that contacted the cathode diffusion layer. These flow channels each had a cavity portion with a width of 1 mm and a flow channel depth of 0.5 mm, and were formed in a straight shape with a spacing between flow channels of 1 mm, with the flow channels running in a direction parallel to the vertical direction when the organic chemical hydride production apparatus was installed. A liquid header combining the plurality of flow channels and used for supply or discharge of the liquid was provided in the structure at each end of the flow channels, and these liquid headers were connected to the pathways for supplying and discharging the organic substances.

Using an expanded mesh having a thickness of 1.0 mm, a distance between centers in the short direction of 3.5 mm and a distance between centers in the long direction of 6.0 mm as the anode substrate, an anode catalyst layer of iridium oxide and tantalum oxide having the same composition as that described in Example 1 was formed on the anode substrate in an amount equivalent to an Ir content per unit area of the anode of 12 g/m$^2$, thus completing the anode.

An elastic body prepared by processing a Ti plate of thickness 0.3 mm to form a shape in which flat springs were aligned at a pitch of 10 mm was used as the anode-supporting elastic body. A very fine platinum layer was formed on the anode contact surfaces of these flat springs.

These cell members, namely the cathode support, the cathode-electrolyte membrane composite, the anode and the anode-supporting elastic body were stacked in that sequence, and by inserting the anode-supporting elastic body between the anode-side partition plate and the anode, the resulting pressing force from the anode side pressed each of the layers into close contact within the fixed cell width.

Toluene was introduced into the cathode chamber of the thus obtained organic chemical hydride production apparatus, a 5% sulfuric acid aqueous solution was introduced into the anode chamber, the apparatus was connected to a constant-current power supply, and the electrolysis reaction described below was performed. The circulation flow rate for each fluid was set so that the linear rate at the cathode side was 1 m/min, and the linear rate at the anode side was 3 m/min. At a cell temperature of 60° C. and 400 mAcm$^{-2}$, the cell voltage was 2.10 V. The current efficiency of the methylcyclohexane at the cathode side was 95%.

The present invention is in no way limited by the embodiments described above, and all manner of modifications such as design alterations may be implemented based on the knowledge of a person skilled in the art, with the resulting embodiments incorporating these implemented modifications also being included within the scope of the present invention.

DESCRIPTION OF THE REFERENCE SIGNS

10: Electrode catalyst-containing anode (Anode)
10a: Anode substrate
10b: Anode catalyst layer
10c: Intermediate layer
10d: Anode-supporting elastic body
11: Solid polymer electrolyte membrane (Electrolyte membrane)
12: Cathode
12a: Cathode substrate
12b: Cathode catalyst layer
12c: Cathode support
13: Cathode chamber
13a: Partition plate
13b: Spacer
14: Anode chamber
14a: Partition plate
14b: Spacer
15: Anode spacer
16: Inlet for substance to be hydrogenated
17: Hydride outlet
18: Acidic electrolytic solution inlet
19: Acidic electrolytic solution outlet
100: Organic chemical hydride-producing electrolytic cell (Electrolytic cell)

The invention claimed is:

1. An anode comprising:
an anode substrate; and
an anode catalyst layer formed on a surface of the anode substrate, wherein
the anode substrate comprises at least one valve metal selected from the group consisting of aluminum, chromium, and titanium, and
the anode catalyst layer comprises $Ir_xTa_yZr_zO_2$, where $x=7$, $y=2$, $z=1$, or $x=7$, $y=1$, $z=2$, so that the anode evolves oxygen in a sulfuric acid aqueous solution containing a substance to be hydrogenated dissolved at a concentration higher than 1 mg/L.

2. The anode for oxygen evolution according to claim 1, wherein an intermediate layer composed of titanium and tantalum is formed between a surface of the anode substrate and the anode catalyst layer.

3. The anode for oxygen evolution according to claim 1, wherein the substance to be hydrogenated is toluene and a main product is methylcyclohexane.

4. The anode for oxygen evolution according to claim 1, wherein the anode substrate comprises titanium.

* * * * *